United States Patent [19]
Fujita

[11] Patent Number: 5,482,042
[45] Date of Patent: Jan. 9, 1996

[54] MEDICAL IMAGING APPARATUS

[75] Inventor: Hidehiro Fujita, Ootawara, Japan

[73] Assignee: Kabushiki Kaisha Toshiba, Kawasaki, Japan

[21] Appl. No.: 269,024

[22] Filed: Jun. 30, 1994

[30]  Foreign Application Priority Data

Jul. 7, 1993  [JP]  Japan .................. 5-167883

[51] Int. Cl.$^6$ ................................. A61B 5/055
[52] U.S. Cl. ................... 128/653.1; 128/653.2; 128/653.5; 128/721
[58] Field of Search ............... 128/653.1, 653.2, 128/653.5, 660.02, 670, 671, 716, 721

[56]  References Cited

U.S. PATENT DOCUMENTS

| | | | |
|---|---|---|---|
| 3,993,995 | 11/1976 | Kaplan et al. | 128/653.1 |
| 4,182,311 | 1/1980 | Seppi et al. | 128/653.1 |
| 4,724,386 | 2/1988 | Haacke et al. | 128/653.2 |
| 4,779,620 | 10/1988 | Zimmermann et al. | 128/653.2 |
| 4,994,743 | 2/1991 | Glover et al. | 128/721 |
| 5,107,846 | 4/1992 | Atlas | 128/721 |
| 5,220,922 | 6/1993 | Barany | 128/721 |
| 5,242,455 | 9/1993 | Skeens et al. | 128/653.1 |
| 5,273,036 | 12/1993 | Kronberg et al. | 128/666 |
| 5,363,844 | 11/1994 | Riederer et al. | 128/653.2 |

FOREIGN PATENT DOCUMENTS

| | | | |
|---|---|---|---|
| 2604890 | 4/1988 | France | 128/653.5 |
| 1-16495 | 3/1989 | Japan . | |

*Primary Examiner*—Krista M. Zele
*Attorney, Agent, or Firm*—Oblon, Spivak, McClelland, Maier & Neustadt

[57]  ABSTRACT

A medical imaging apparatus comprises a respiration depth detecting device for detecting a respiration depth of a subject and an indication device for indicating the respiration depth determined by the respiration depth detecting device to the subject. The respiration depth detecting device includes a measuring device for measuring a position of the surface of the body of the subject, a device for detecting a maximum value and a minimum value of the respiration depth of the subject on the basis of maximum extreme values and minimum extreme values of the position of the surface of the body measured by the measuring device, and a device for calculating the respiration depth of the subject on the basis of the position of the surface of the body measured by the measuring device and the maximum value and minimum value of the respiration depth. The indication means includes a plurality of light emitting elements, and a device for turning on at least one of the light emitting elements in accordance with the respiration depth of the subject.

1 Claim, 4 Drawing Sheets

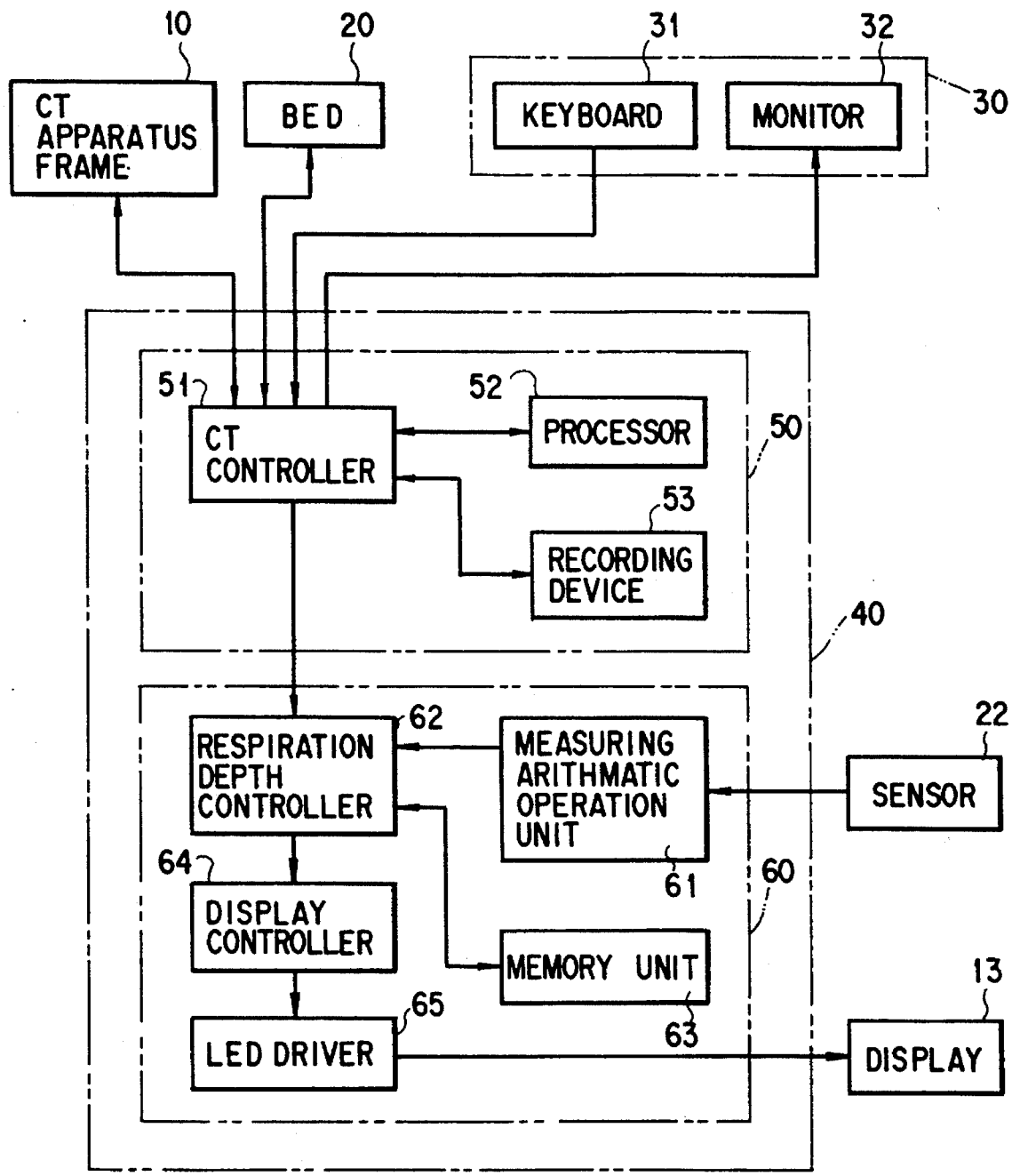
F I G. 3

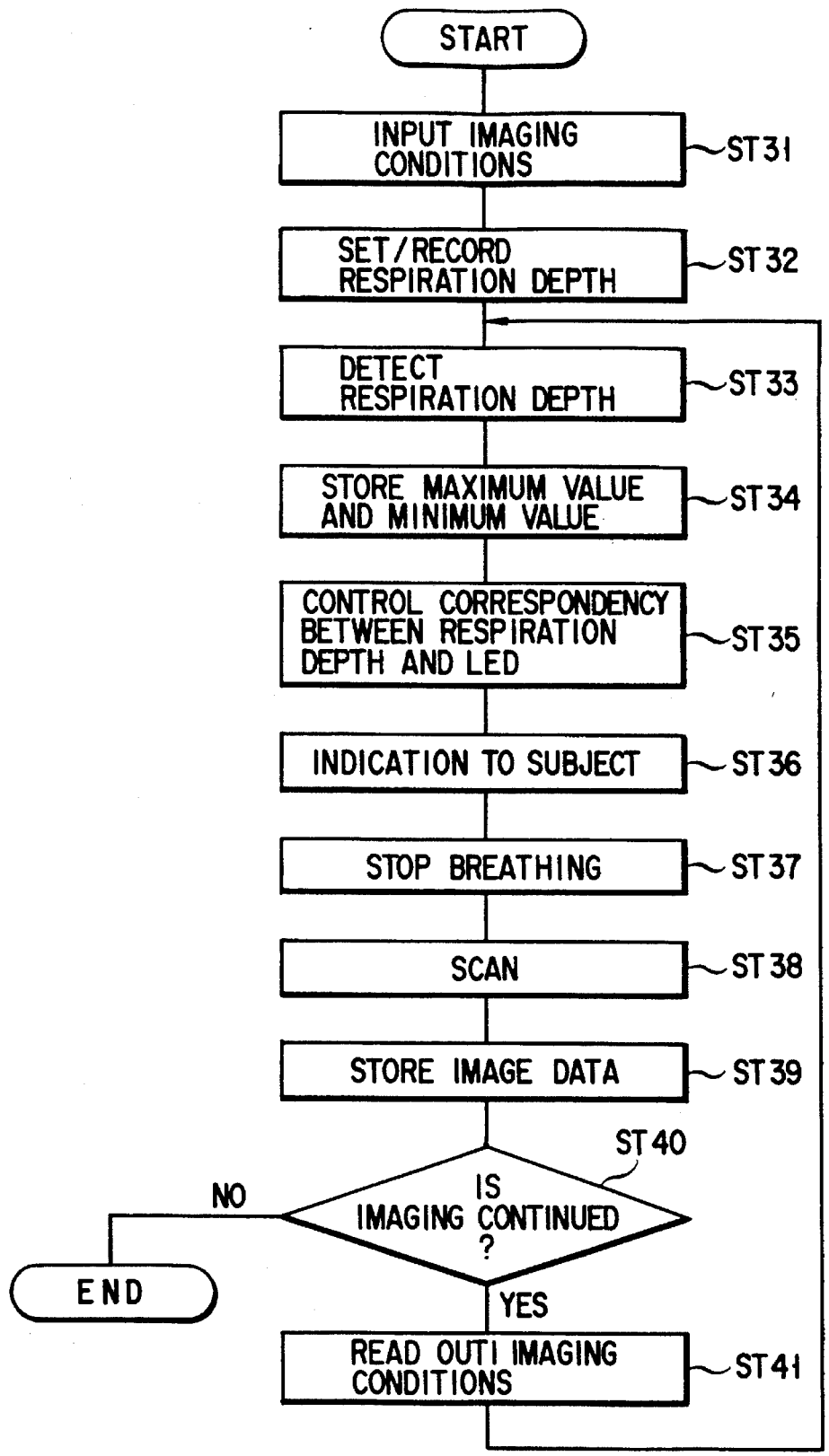
F I G. 5

MEDICAL IMAGING APPARATUS

BACKGROUND OF THE INVENTION

1. Field of the Invention

The present invention relates generally to a medical imaging apparatus and more particularly to an X-ray computer tomograph (hereinafter referred to as "X-ray CT apparatus") for imaging a subject in synchronism with the respiration of the subject.

2. Description of the Related Art

There is a well-known conventional method of acquiring a tomographic image of a subject placed on a bed by means of an X-ray CT apparatus or one of medical imaging apparatus. With the X-ray CT apparatus, an operator operates a control table to slide a movable top plate provided above the bed and to introduce the subject into an opening formed in a central portion of a CT apparatus frame having an imaging device comprising an X-ray tube. After the top plate is situated at a predetermined position, a scanning operation of a predetermined scanning system is performed. An image is reconstructed on the basis of acquired image data, and an image is displayed on a monitor.

The scanning system is classified into two systems: 1) a single scan system in which image data of one tomogram is acquired with the top plate kept stationary, and 2) a multi-scan system in which image data of many tomograms is obtained by a single operation. Further, the multi-scan system is classified into two systems: 1) a helical scan system in which image data is acquired helically along the axis of a subject, and 2) a rapid scan system in which image data is acquired by repeating at short time intervals the above-mentioned single scan system and the movement of the top plate. A three-dimensional (3D) image is formed based on many tomograms obtained by the multi-scan system.

In the X-ray CT apparatus, an artifact may appear in an image due to movement of the subject during scanning. In any of the scan systems, therefore, the subject must hold this breath from the beginning to the end of the scan. In the case where locations to be imaged are present in a wide area, if the subject takes a breath during the scan operation, the scan operation must be suspended. Then, the subject holds his breath once again and the scanning operation is resumed from the location at which the scan operation was suspended due to the breathing of the subject.

The above conventional X-ray CT apparatus has the following problem. The positional relationship between the subject's muscles and internal organs varies according to the state of respiration (hereinafter referred to as "respiration depth") of the subject. Thus, the subject must make constant the respiration depth before and after the breathing spell. However, since the respiration depth is determined by the subject's sensation, it is very difficult for the subject to make exactly constant the respiration depth before and after the breathing spell.

If the subject takes a breath during acquiring image data in the helical scan system, image data becomes discontinuous before and after the breathing spell, and it is not possible to form a tomogram of an area including a location at which the scan operation was suspended due to the breathing spell. Consequently, the scan operation must be performed once again from the beginning, and the amount of radiation applied to the subject increases.

In the case where a plurality of tomograms are formed on the basis of projection image data obtained by the multi-scan system (e.g. rapid scan system), if the positional relationship between the internal organs varies before and after the respiration spell, an object such as an ulcer, which is smaller than the internal organs, may move in a direction perpendicular to a slice plane in some cases. Thus, it may be possible that the object does not appear on a tomogram or the size of the object is not exactly determined.

When a 3D image is constructed from many tomograms obtained by the multi-scan system, discontinuity may appear on a 3D image between locations imaged before and after the breathing spell and the obtained 3D image becomes unnatural.

On the other hand, in the case where tomograms of a specified location of the subject are taken at regular time intervals in order for a doctor to diagnose the healing condition of the affected part before and after a surgical operation, the positional relationship between the internal organs, etc. varies if the respiration depth varies. As a result, exact observation and diagnosis cannot be performed.

In addition to the above X-ray CT apparatus, other medical imaging apparatus have the same problems.

SUMMARY OF THE INVENTION

The present invention has been made in order to solve the above problems.

A first object of the invention is to provide a medical imaging apparatus wherein in the case of acquiring projection data continuously, the positional relationship among the internal organs of a subject can be made constant before and after a breathing spell of the subject, thereby acquiring continuous projection data and obtaining an image of a desired location in a scanning scope.

A second object of the invention is to provide a medical imaging apparatus wherein in the case of comparing a plurality of images, the positional relationship among the internal organs of a subject can be made constant before and after a breathing spell of the subject, thereby exactly determining the presence/absence and/or size of a small object such as an ulcer.

A third object of the invention is to provide a medical imaging apparatus wherein in the case of constructing a three-dimensional (3D) image by forming based on a plurality of images, the positional relationship among the internal organs of a subject can be made constant before and after a breathing spell of the subject, thereby acquiring a 3D image having no unnatural image portion due to discontinuity between images obtained before and after the breathing spell.

A fourth object of the invention is to provide a medical imaging apparatus wherein in the case of acquiring an image of a specified location in a subject once again after a predetermined time period, the positional relationship among the internal organs of a subject can be made constant before and after a breathing spell of the subject, thereby exactly diagnosing the healing condition of an affected part and the condition of permeation of a medicine.

According the present invention, there is provided an apparatus for acquiring a medical image of a subject, comprising: respiration depth detecting means for detecting a respiration depth of the subject; and indication means for indicating the respiration depth detected by the respiration depth detecting means to the subject.

According to this invention, in the case of acquiring projection data continuously, the positional relationship among the internal organs of a subject can be made constant before and after a breathing spell of the subject, thereby acquiring continuous projection data and obtaining an image of a desired location in a scanning scope.

In addition, in this invention, in the case of comparing a plurality of images, the positional relationship among the internal organs of a subject can be made constant before and after a breathing spell of the subject, thereby exactly determining the presence/absence and/or size of a small object such as an ulcer.

According to this invention, in the case of constructing a three-dimensional (3D) image by super-imposing a plurality of images, the positional relationship among the internal organs of a subject can be made constant before and after a breathing spell of the subject, thereby acquiring a 3D image having no unnatural image portion due to discontinuity between images obtained before and after the breathing spell.

According to this invention, in the case of acquiring an image of a specified location in a subject once again after a predetermined time period, the positional relationship among the internal organs of a subject can be made constant before and after a breathing spell of the subject, thereby exactly diagnosing the healing condition of an affected part and the condition of permeation of a medicine.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 3 is a block diagram showing the structure of a control apparatus built in the X-ray CT apparatus according to the first embodiment;

FIG. 5 is a flow chart illustrating a process of acquiring projection data at predetermined time intervals with the X-ray CT apparatus according to the first embodiment.

DETAILED DESCRIPTION OF THE PREFERRED EMBODIMENTS

Figure 1:
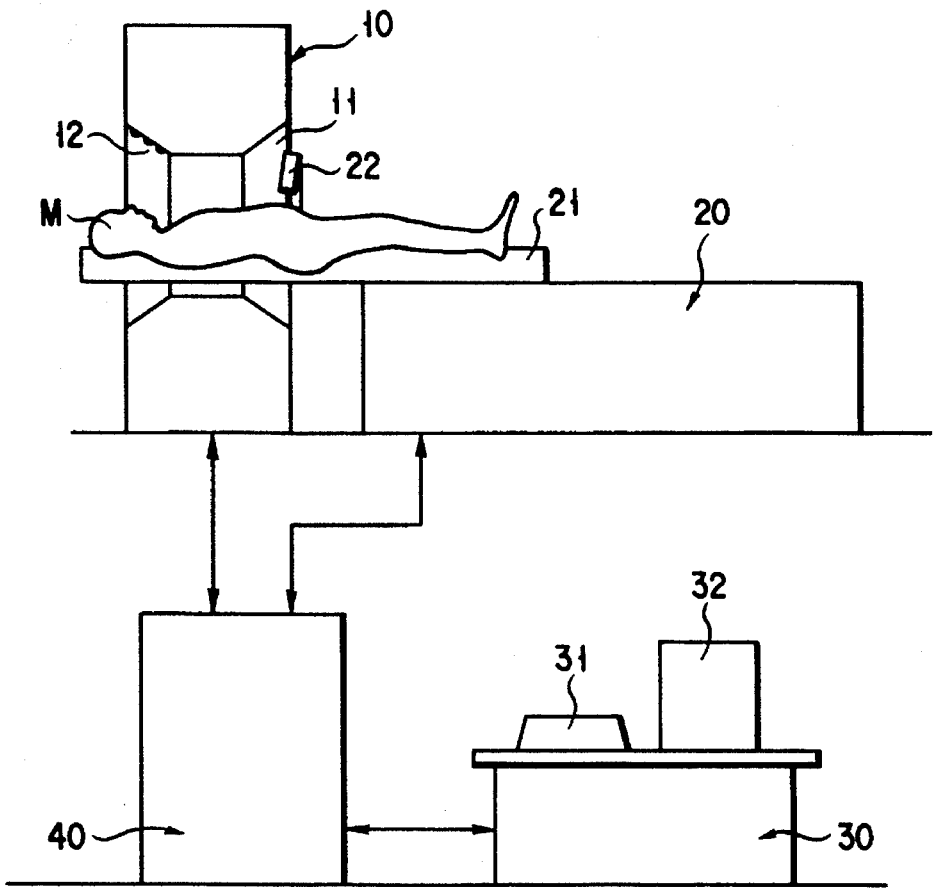
FIG. 1 shows schematically the structure of an X-ray CT apparatus according to a first embodiment of the present invention.
Figure 2:
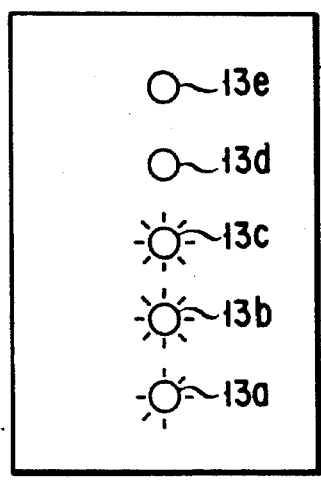
FIG. 2 is a front view of an LED display built in the X-ray CT apparatus according to the first embodiment of the invention.

FIG. 1 shows schematically the structure of an X-ray CT apparatus or an example of a medical imaging apparatus according to a first embodiment of the present invention, FIG. 2 is a front view of an LED display built in the X-ray CT apparatus, FIG. 3 is a block diagram showing the structure of a control apparatus built in the X-ray CT apparatus.

In FIG. 1, reference numeral 10 denotes a CT apparatus frame, numeral 20 denotes a bed, 30 denotes a control table, and 40 denotes a control apparatus. The CT apparatus frame 10 contains an imaging apparatus composed of, e.g. an X-ray tube, etc. An opening 11, in which a subject M is introduced, is formed in a center portion of the frame 10. The opening 11 is provided with a display 12. The display 12 comprises five linearly arranged LEDs 13a to 13e, which are turned on according to the respiration depth, as is shown in FIG. 2. The LEDs 13a to 13e are controlled by an LED driving circuit 65. The LEDs 13a, 13b, 13d and 13e emit green light and the LED 13c emits red light. The subject M is placed on the bed 20. A top plate 21 is slidably supported on the bed 20 so as to introduce the subject M into the opening 11 in the CT apparatus frame 10. The top plate 21 is provided with an ultrasonic sensor 22 for detecting a distance between itself and the surface of the body of the subject M. The control table 30 is provided with a keyboard 31, by which an operator inputs imaging conditions, etc., and a monitor 32 for displaying images such tomograms and the respiration depth like the LEDs 13a to 13e.

As is shown in FIG. 3, the control apparatus 40 comprises a CT control device 50 and a respiration depth control device 60. The CT control device 50 controls the operations of the imaging apparatus provided in the CT apparatus frame 10 and the bed 50 and processes input data from the keyboard 31 and projection data. The respiration depth control device 60 controls the respiration depth of the subject M.

The CT control device 50 comprises a CT controller 51 connected to the CT apparatus frame 10, bed 20, keyboard 31 of control table 30 and monitor 32, a processor 52, connected to the CT controller 51, for reconstructing a tomogram from projection data from the CT apparatus frame 10, and a recording device 53, connected to the CT controller 51, for recording projection data, image data, etc. The CT controller 51 can perform scans of various systems, such as a single scan, a helical scan and a rapid scan, according instructions from the operator. The CT controller 51 is connected to a respiration depth controller 62 (described later).

The respiration depth control unit 60 comprises a measuring arithmetic operation unit 61 for measuring the respiration depth on the basis of an output from the ultrasonic sensor 22; a respiration depth controller 62, connected to an output terminal of the measuring arithmetic operation unit 61, for controlling the respiration depth; a memory unit 63, connected to the respiration depth controller 62, for storing a maximum value and a minimum value of the respiration depth; a display controller 64, connected to the respiration depth controller 62, for controlling correspondency between the respiration depth and the display by the LEDs 13a to 13e; and an LED driver 65, connected to the display controller 64, for driving the LEDs 13a to 13e on the basis of a signal from the display controller 64.

The operation for acquiring projection data by a helical scan system by using the X-ray CT apparatus having the above structure according to the present embodiment will now be described with reference to the flow chart of FIG. 3. In the following description, "ST" means "step."

At first the subject M lies on the top plate 21. The operator inputs imaging conditions such as an imaging range or a stroke of the top plate 21 and X-ray conditions (X-ray tube current, X-ray tube voltage, etc.) from the keyboard 31 (ST1). Then, the top plate 21 is slid and the subject M is moved to the scan start point in the opening 11 of the CT apparatus frame 10. Subsequently, the operator manipulates the keyboard 31 to set the CT controller 51 of the CT control device 50 and the respiration depth controller 62 of the respiration depth control device 60 in a respiration depth measuring mode. The operator instructs the subject M to take a deep breath. At this time, the ultrasonic sensor 22 measures the distance between itself and the surface of the belly of the subject M (ST2). If the deep breath is repeated, the distance between the sensor 22 and the surface of the belly of the subject M varies. When the subject M inhales a maximum amount of air, the distance takes a minimum extreme value, and when the subject M exhales a maximum amount of air, the distance takes a maximum extreme value. On the basis of the output from the ultrasonic sensor 22, the measuring arithmetic operation unit 61 measures an average value of the maximum extreme values of the distance and an average value of the minimum extreme values of the distance. The average value of the maximum extreme values of the distance and the average value of the minimum extreme values of the distance are stored in the memory unit 63 via the respiration depth controller 62 as a maximum distance value and a minimum distance value (ST3). The maximum value and minimum value are read out from the memory unit 63 by the respiration depth controller 62 and input to the display controller 64. In addition, a current distance value between the sensor 22 and the surface of the body of the subject M, which is measured by the sensor 22, is input to the display controller 64. The display controller 64 controls the correspondency between the respiration depth of the subject M and LEDs 13a to 13e on the basis of the maximum value, minimum value and current value, thereby displaying the respiration depth (ST4). Specifically, the total range between the maximum value and minimum value is divided into five sub-ranges. When the distance takes the maximum value, all LEDs 13a to 13e are turned off. When the distance is in a sub-range between the maximum value and 1/5 of the total range from the maximum value, only the LED 13a is turned on. When the distance is in a sub-range between the 1/5 of the total range from the maximum value and 2/5 of the total range from the maximum value, the LEDs 13a and 13b are turned on. In this manner, the number of LEDs to be turned on is increased successively. Based on the control by the display controller 64, the LED driver 65 drives the LEDs 13a to 13e. When the subject M has exhaled completely, i.e. when the respiration depth is minimum, all LEDs 13a to 13e are turned off. As the amount of inhaled air increases, the LEDs are successively turned on from the LED 13a. When the subject M has inhaled the maximum amount of air, i.e. when the respiration depth is maximum, all LEDs 13a to 13e are turned on. As the amount of exhaled air increases, the LEDs are successively turned off from the LED 13e.

Then, the operator switches the respiration depth measuring mode to the imaging mode by manipulating the keyboard 31. The operator sets the respiration depth for imaging at, e.g. an intermediate respiration depth (ST5). The operator instructs the subject M to stop breathing when the red LED 13c corresponding to the intermediate respiration depth is turned on (ST6). Since the intermediate respiration depth is normally easy for the subject M, the subject M can stop breathing for a relatively long time. The subject M takes a deep breath several times while viewing the LEDs 13a to 13e of the display 12 when the red LED 13c is turned on, the subject M stops breathing (ST7). The operator confirms, by the display on the monitor 32, that the subject M stops breathing while the LED 13c is being turned on, and inputs a scan start command from the keyboard 31 (ST8). During the scan operation, it is determined whether the scan of the entire stroke has been completed (ST9). When the scan is completed, the scan is automatically stopped (ST10) and the acquisition of projection data is finished. At this time, the projection data as well as tomographic images and associated information is recorded in the recording device 53 as image data (ST11). The associated information includes the date of imaging, the name of the subject, the sex of the subject, the age of the subject, X-ray conditions (X-ray tube current, X-ray tube voltage, etc.), the scope of imaging, the respiration depth, etc.

On the other hand, if the scan of the entire stroke has not been completed ("NO" in ST9), it is determined whether the subject M has taken a breath (ST12). Even in the imaging mode, the ultrasonic sensor 22 is detecting the distance between the sensor 22 and the surface of the body of the subject M. Accordingly, if the subject M takes a breath, a variation in distance is input to the respiration depth controller 62 via the measuring arithmetic operation unit 61. The respiration depth controller 62 delivers a halt signal to the CT controller 51, and the CT controller 51 issues a scan halt command to the CT apparatus frame 10 (ST13). After the scan halt, the control returns to ST6. After passage of an appropriate time period, the operator instructs the subject M to take a deep breath and stop breathing once again when the red LED 13c is turned on. After confirming that the subject M has stopped breathing when the red LED 13c was turned on, the operator inputs a scan resume command to the keyboard 31. The scan is resumed from the location at which the scan was suspended due to the breath of the subject M. In this manner, this process is repeated until the imaging of the entire stroke is completed. After the completion of imaging, the operator designates a predetermined slice plane in the subject M by manipulating the keyboard 31, and a tomogram is reconstructed by the processor 52 and displayed on the monitor 32.

In the above embodiment, since the respiration depth can be equalized before and after the breathing spell, the positional relationship of the internal organs, etc. is made substantially constant, and continuous projection data can be obtained. Thus, during the helical scan operation, tomograms obtained before and after the breathing spell can be reconstructed.

A plurality of tomograms can be reconstructed on the basis of projection data acquired by the helical scan or projection data acquired by the rapid scan in the similar procedures. Suppose that adjacent tomograms reconstructed from the projection data acquired by the rapid scan or helical scan are observed. In this case, by making the respiration depth constant, an object to be imaged is prevented from moving vertically in the slice plane of the tomograms. Thus, the presence/absence or size of a relatively small object such as an ulcer can be diagnosed. Therefore, an exact diagnosis can be performed. Moreover, even if a 3D image is produced from many tomograms, unnatural discontinuity does not appear at the location imaged when the subject took a breath.

FIG. 5 is a flow chart illustrating a process of obtaining at regular time intervals tomograms of a specified location on the subject M so that a doctor may diagnose the healing condition or the permeation of a medicine in an affected part of the subject M who was subjected to a surgical operation.

A process of confirming the healing condition of the affected part of the subject M every few days will now be described. The subject M lies on the top plate 21. The operator inputs imaging conditions such as an imaging location and X-ray conditions (X-ray tube current, X-ray tube voltage, etc.) from the keyboard 31 (ST31). Then, the top plate 21 is slid and the subject M is moved to the scan start point in the opening 11 of the CT apparatus frame 10. Subsequently, the operator determines the respiration depth at the time of imaging the operator and records the respiration depth in the recording device as part of associated information (ST32). The operator manipulates the keyboard 31 to set the CT controller 51 of the CT control device 50 and the respiration depth controller 62 of the respiration depth control device 60 in a respiration depth measuring mode. The operator instructs the subject M to take a deep breath. At this time, the ultrasonic sensor 22 measures the distance between itself and the surface of the belly of the subject M (ST33). If the deep breath is repeated, the distance between the sensor 22 and the surface of the belly of the subject M varies. When the subject M inhales a maximum amount of air, the distance takes a minimum extreme value, and when the subject M exhales a maximum amount of air, the distance takes a maximum extreme value. On the basis of the output from the ultrasonic sensor 22, the measuring arithmetic operation unit 61 measures an average value of the maximum extreme values of the distance and an average value of the minimum extreme values of the distance. The average value of the maximum extreme values of the distance and the average value of the minimum extreme values of the distance are stored in the memory unit 63 via the respiration depth controller 62 as a maximum distance value and a minimum distance value (ST34). The maximum value and minimum value are read out from the memory unit 63 by the respiration depth controller 62 and input to the display controller 64. In addition, a current distance value between the sensor 22 and the surface of the body of the subject M, which is measured by the sensor 22, is input to the display controller 64. The display controller 64 controls the correspondency between the respiration depth of the subject M and LEDs 13a to 13e on the basis of the maximum value, minimum value and current value, thereby displaying the respiration depth (ST35). Specifically, the total range between the maximum value and minimum value is divided into five sub-ranges. When the distance takes the maximum value, all LEDs 13a to 13e are turned off when the distance is in a sub-range between the maximum value and 1/5 of the total range from the maximum value, only the LED 13a is turned on when the distance is in a sub-range between the 1/5 of the total range from the maximum value and 2/5 of the total range from the maximum value, the LEDs 13a and 13b are turned on. In this manner, the number of LEDs to be turned on is increased successively. Based on the control by the display controller 64, the LED driver 65 drives the LEDs 13a to 13e. When the subject M has exhaled completely, i.e. when the respiration depth is minimum, all LEDs 13a to 13e are turned off. As the amount of inhaled air increases, the LEDs are successively turned on from the LED 13a. When the subject M has inhaled the maximum amount of air, i.e. when the respiration depth is maximum, all LEDs 13a to 13e are turned on. As the amount of exhaled air increases, the LEDs are successively turned off from the LED 13e.

Then, the operator switches the respiration depth measuring mode to the imaging mode by manipulating the keyboard 31. The operator instructs the subject M to stop breathing when the red LED 13c corresponding to the intermediate respiration depth is turned on (ST36). Since the intermediate respiration depth is normally easy for the subject M, the subject M can stop breathing for a relatively long time. The subject M takes a deep breath several times while viewing the LEDs 13a to 13e of the display 12. When the red LED 13c is turned on, the subject M stops breathing (ST37). The operator confirms that the subject M stops breathing while the LED 13c is being turned on, and inputs a scan start command from the keyboard 31 to start the scan (ST38). Since the location of imaging is limited, the scan can be completed in a short time period. The projection data acquired at this time is reconstructed by the processor 52 and displayed on the monitor as a tomographic image. The tomographic image as well as associated information is recorded in the recording device 53 as image data (ST39). The operator inputs a command representing whether the imaging should be continued or not. If further imaging is not necessary, the imaging is finished (ST40).

On the other hand, if the imaging is continued, the subject M is placed on the top plate 21 once again after several days. In this case, in order to employ the same imaging conditions as the previous ones, the imaging conditions are read out from the recording device 53 and set in the CT controller 51 (ST41). After the imaging conditions are set, the control returns to ST32 and the respiration depth is measured in the same manner as described above. In most cases, the distance between the ultrasonic sensor 22 and the surface of the body of the subject M differs from the previously set one. In this connection, the weight of the subject M may vary in several days. However, if the respiration depth at the time of imaging is made constant, the positional relationship among the internal organs, etc. does not greatly vary. In step ST35, the operator performs an imaging operation with the same respiration depth as was recorded previously as image data. If a necessary number of projection images have been acquired, the imaging is finished.

After the completion of the imaging, the doctor compares tomograms of the subject M obtained every few days and diagnoses the healing condition of the affected part. In this case, since the positional relationship among the internal organs, etc. is substantially constant, the tomograms obtained every few days can be easily compared and observed and the healing condition of the internal organs, etc. can be easily understood. Therefore, an exact diagnosis can be performed.

Figure 6:
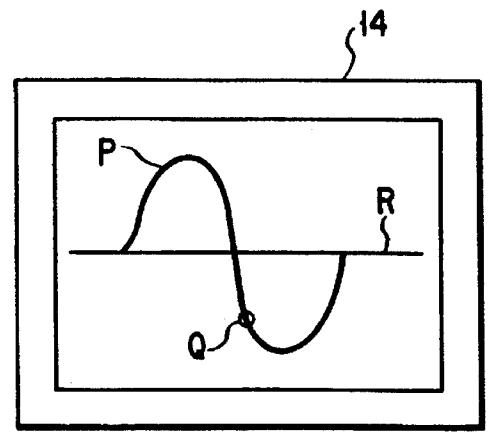
FIG. 6 shows a monitor screen built in the X-ray CT apparatus according to the first embodiment.
Figure 4:
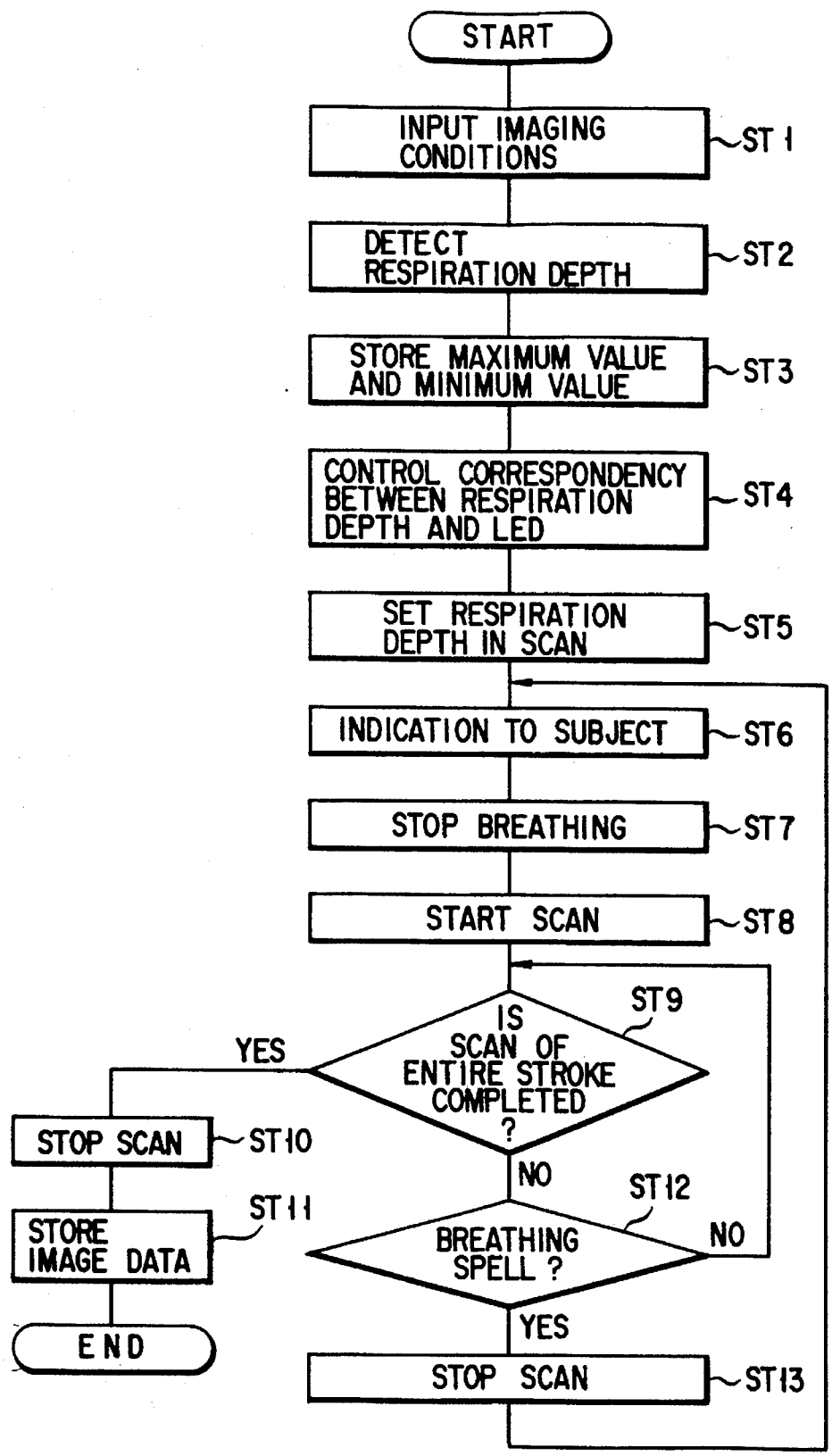
FIG. 4 is a flow chart illustrating a process of acquiring wide-range projection data with the X-ray CT apparatus according to the first embodiment.

The present invention is not limited to the above embodiment. Although the ultrasonic sensor is used to sense the movement of the body, it may be replaced by a compression cylinder. Moreover, as another method of indicating the respiration depth, a monitor 14 as shown in FIG. 6 may be used. On the monitor 14, one cycle of a variation of the measured respiration depth is expressed as a graph P or a time-basis variation. A current value Q is indicated on the graph P, and the subject M is instructed to stop breathing at a predetermined point R. In addition, a voice synthesis IC may be used to instruct the subject M to stop breathing by a synthetic voice. Although the present invention is applied to the X-ray CT apparatus in the above embodiment, it may be applied to other medical imaging apparatus. Needless to say, other various modifications may be made without departing from the spirit of the present invention.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An apparatus for acquiring a medical image of a subject, comprising:

respiration depth detecting means for detecting a respiration depth of the subject;

indication means for indicating the respiration depth detected by said respiration depth detecting means to the subject;

image acquiring means for acquiring a predetermined image of the subject only during a time when the subject holds its breath in accordance with the indicated respiration depth by the indication means;

storage means for storing the respiration depth of the subject; and read means for reading out the respiration depth of the subject from the storage means.

* * * * *